United States Patent [19]

Nakanishi et al.

[11] Patent Number: 4,665,200
[45] Date of Patent: May 12, 1987

[54] METHOD FOR PREPARING PYROMELLITIC ACID AND/OR PYROMELLITIC ANHYDRIDE

[75] Inventors: Yoshiyuki Nakanishi; Yoji Akazawa; Ikuo Kurimoto; Youjirou Takahashi; Shinichi Uchida; Hisashi Yoshikawa, all of Himeji, Japan

[73] Assignee: Nippon Shokubai Kagaku Kogyo Co., Ltd., Osaka, Japan

[21] Appl. No.: 841,833

[22] Filed: Mar. 20, 1986

Related U.S. Application Data

[63] Continuation-in-part of Ser. No. 736,379, May 21, 1985, abandoned.

[30] Foreign Application Priority Data

May 21, 1984 [JP] Japan ................................ 59-100577
Jul. 17, 1984 [JP] Japan ................................ 59-146886
Jul. 18, 1984 [JP] Japan ................................ 59-147641

[51] Int. Cl.$^4$ ............................................. C07D 307/89
[52] U.S. Cl. .................................... 549/239; 502/209; 562/415
[58] Field of Search .......................... 549/239; 562/415

[56] References Cited

U.S. PATENT DOCUMENTS

| | | | |
|---|---|---|---|
| 3,255,211 | 1/1966 | Kerr ................................ | 502/209 X |
| 3,684,741 | 8/1972 | Friedrichsen et al. .............. | 502/209 |
| 3,870,655 | 3/1975 | Nanba et al. ........................ | 502/209 |
| 3,926,846 | 12/1975 | Ono et al. ............................ | 502/179 |
| 4,046,780 | 9/1977 | Nakanishi et al. ............... | 502/209 X |
| 4,077,912 | 3/1978 | Dolhyj et al. ........................ | 502/179 |
| 4,324,694 | 4/1982 | Reuter et al. ........................ | 502/209 |
| 4,356,112 | 10/1982 | Nakanishi et al. .................. | 502/179 |
| 4,481,304 | 11/1984 | Sato et al. ............................ | 502/209 |

FOREIGN PATENT DOCUMENTS 20302 5/1974 Japan .
31972 8/1974 Japan .
49-41036 11/1974 Japan .
50-39292 4/1975 Japan .

Primary Examiner—Richard L. Raymond
Attorney, Agent, or Firm—Sherman and Shalloway

[57] ABSTRACT

In a method for the preparation of pyromellitic acid or its anhydride by catalytic vapor phase oxidation of a tetra-$C_1$-$C_4$-alkylbenzene using a catalyst comprising catalytically active material composed of 1 to 20 parts by weight of $V_2O_5$, 99 to 80 parts by weight of $TiO_2$ and/or $SnO_2$ and/or $ZrO_2$, and per one hundred parts by weight of $V_2O_5$, $TiO_2$ and/or $SnO_2$ and/or $ZrO_2$ 0.02 to 10 parts by weight, calculated as $P_2O_5$, of a phosphorus compound, 0.01 to 5 parts by weight, calculated as $Nb_2O_5$, of a niobium compound, 0 to 1.2 parts by weight, calculated as oxide, of at least one metal selected from the group consisting of potassium, cesium, rubidium and thallium, and 0 to 10 parts by weight, calculated as $Sb_2O_3$, of an antimony compound, and an inert carrier supporting said catalytically active material thereon, the improvement in which said catalyst is divided into at least two layers, a layer on the gas inlet side and a layer on the gas outlet side, and (i) the content of potassium, cesium, rubidium or thallium is higher in the catalyst layer on the gas inlet side than in the catalyst layer on the gas outlet side, or (ii) the content of the phosphorus compound is lower in the catalyst layer on the gas inlet side than in the catalyst layer on the gas outlet side, or (iii) the surface area of $TiO_2$ and/or $SnO_2$ and/or $ZrO_2$ is lower in the catalyst layer on the gas inlet side than in the catalyst layer on the gas outlet side.

14 Claims, No Drawings

METHOD FOR PREPARING PYROMELLITIC ACID AND/OR PYROMELLITIC ANHYDRIDE

This application of U.S. Ser. No. 736,379 filed on May 21, 1985, now abandoned.

This invention relates to a method for preparing pyromellitic acid and/or pyromellitic anhydride by vapor phase catalytic oxidation of a tetra-$C_1$-$C_4$-alkylbenzene such as durene with air or a molecular oxygen-containing gas.

Vapor-phase catalytic oxidation of tetra-$C_1$-$C_4$-alkylbenzenes such as durene with air or a molecular oxygen-containing gas is one of the industrial methods to obtain pyromellitic acid or pyromellitic anhydride. Although a number of catalysts have been proposed for this oxidation process, none of them have proved to have satisfactory performances. For instance, the catalysts proposed in Japanese Patent Publications Nos. 20302/1974 and 31972/1974 show relatively high yields in the preparation of pyromellitic anhydride by vapor phase oxidation of durene. However, these high yields are achieved only under the conditions of a very low concentration of durene in a feed gas and of a very high space velocity. To use catalysts which have to be operated under such conditions is disadvantageous for the industrial oxidation process because the lower ratio of durene/air requires more energy to send a reaction gas to a reactor and higher space velocities result in an increased pressure drop of the catalyst bed.

The industrial oxidation process where the concentration of a hydrocarbon to be oxidized in a feed gas is extremely low has another problem that a heat medium surrounding catalyst packed tubes in a reactor has to be heated by an external heating apparatus in order to maintain an optimum reaction temperature because the latent heat of the feed gas through the reactor exceeds the total oxidation heat of the hydrocarbon.

On the other hand, it is generally considered advantageous for industrial practice to use catalysts at higher space velocities because the catalyst volume needed becomes smaller. However, in a practical multi-tube reactor the catalyst bed packing length must be more than 1,000 mm, preferably more than 1,500 mm in view of the reactor design and a heat removal system for the reactor. For this reason, there is a limitation in decreasing the catalyst volume in a tube of a practical industrial reactor, and the pressure drop of a catalyst bed becomes extremely high as the linear velocity of the gas in the tube is very high at such a high space velocity. As above said, the catalytic oxidation reaction carried out under the conditions of low concentrations of a hydrocarbon to be oxidized in a feed gas and of high space velocities is not always economical in a commercial operation because it leads the increase of steam or electricity in loading on an air blower or compressor.

Accordingly, the objective of this invention is to provide catalysts for the preparation of pyromellitic acid and/or pyromellitic anhydride by the vapor phase fixed bed catalytic oxidation of a tetra-$C_1$-$C_4$-alkylbenzene such as durene with air or a molecular-oxygen-containing gas which have a high selectivity to pyromellitic acid and/or pyromellitic anhydride and high heat durability in an operation under high loading conditions of high ratios of the tetra-alkylbenzene/air or molecular oxygen-containing gas, 20-60 g/$NM^3$, and of relatively low space velocities of 1,000-10,000 $hr^{-1}$.

As a result of investigations on the improvement of the heat durability of catalysts, we have found that a specific supported catalyst on an inert carrier, especially an inert porous carrier, is suitable for the purpose of this invention and this specific catalyst comprises a catalytically active material composed of vanadium pentoxide, titanium dioxide and/or zirconium dioxide and/or stannic dioxide and some other specific ingredients.

It has also been found that the addition of a specific amount of an antimony compound is advantageous for the life of the catalyst because the optimum operating temperature of the catalyst is lower than that of the catalyst without addition of the antimony compound.

This invention is specified as follows:

(1) Supported catalysts on an inert carrier suitable for the preparation of pyromellitic acid or its anhydride by catalytic vapor phase oxidation of a tetra-$C_1$-$C_4$-alkylbenzene, said catalyst comprising a catalytically active material composed of 1–20 parts by weight of $V_2O_5$, 99–80 parts by weight of $TiO_2$ and/or $SnO_2$ and/or $ZrO_2$, and per one hundred parts by weight of $V_2O_5$, $TiO_2$ and/or $SnO_2$ and/or $ZrO_2$ combined, 0.02 to 10 parts by weight, calculated as $P_2O_5$, of a phosphorus compound, 0.01 to 5 parts by weight, calculated as $Nb_2O_5$, of a niobium compound, 0 to 1.2 parts by weight, calculated as oxide, of at least one metal selected from the group consisting of potassium, cesium, rubidium and thallium, 0 to 10 parts by weight, calculated as $Sb_2O_3$, of an antimony compound, and an inert carrier supporting said catalytically active material thereon.

(2) Supported catalysts according to the description (1) where the weight ratio of $TiO_2/SnO_2$ is less than 4.

(3) Supported catalysts according to the description (1) where the weight ratio of $TiO_2$ and/or $SnO_2/ZrO_2$ is less than 4.

Titanium dioxide which is suitable for this invention is anatase prepared by either the pyrolysis of ammonium titanyl sulfate, the calcination of titanium hydroxide obtained by hydrolysis of titanium sulfate, the vapor phase oxidation of titanium tetrachloride, or another method. Porous anatase of which particle size is 0.4–0.7 micron and specific surface area is 10–60 $m^2/g$ obtained by the calcination of titanium hydroxide is used especially preferably.

As stannic dioxide for the purpose of the invention $SnO_2$ prepared by the previous calcination of a stannic or stannous compound as sulfate, nitrate, carbonate and so on is preferably used and $SnO_2$ obtained by calcination of stannous sulfate at a temperature of 600°–900° C. for 2-10 hours and having a particle size of 0.01–1 micron and a specific surface area of 5–100 $m^2/g$, especially 8–60 $m^2/g$, is used especially preferably.

As zirconium dioxide $ZrO_2$ obtained by the calcination of a zirconium compound as sulfate, nitrate, and so on is preferably used and $ZrO_2$ prepared by the calcination of zirconyl nitrate at a temperature of 600°–900° C. for 2-10 hours and having a particle size of 0.01–1 micron and a specific surface area of 5–100 $m^2/g$, especially 8–60 $m^2/g$, is used especially preferably.

The catalyst of the present invention is of the composition comprising $V_2O_5$, $TiO_2$ and/or $SnO_2$ and/or $ZrO_2$, $P_2O_5$, $Nb_2O_5$ and optionally $Sb_2O_3$ and optionally at least one metal oxide selected from the group consisting of $K_2O$, $Cs_2O$, $Rb_2O$ and $Tl_2O$ and further optionally, per 100 parts by weight of $V_2O_5$ and $TiO_2$ and/or $ZrO_2$ and/or $SnO_2$, 0.01–3 parts by weight of at least one compound of the group consisting of CaO, SrO, BaO, ZnO and rare earth element oxides. The term "rare earth element" used in this specification means elements of atomic number 39 and of atomic number 57-71 and preferably Y, La, Ce, Nd, Gd, Tb and Er are used.

The $V_2O_5$, $Nb_2O_5$, $P_2P_5$, $Sb_2O_3$, $K_2O$, $Cs_2O$, $Tl_2O$, $Rb_2O$, CaO, SrO, BaO, ZnO and rare earth element oxides used in the catalyst of the present invention may be adequately chosen from oxides, ammonium salts, nitrates, sulfates, halides, carbonates, hydroxides, organic acid salts and other compounds derived from such elements. That is to say, the components of the catalysts of the present invention are not restricted to the oxides as described in this specification, which indicate merely the compositions of integral constituents in the finished catalyst.

As the carriers, ordinary inert inorganic substances are used for the catalyst of the invention, but suitable porous inert carriers are those having an apparent porosity of 5-50%, a specific surface area of less than 5 $m^2/g$, preferably less than 1 $m^2/g$, a silicon carbide content of more than 50% by weight, preferably more than 80% by weight and an aluminum content calculated as $Al_2O_3$ of less than 10% by weight, preferably less than 3% by weight. Accordingly, self-bonded silicon carbide having a purity of more than 98% is also suitably used for this invention.

The form of the carrier is not limited and a sphere-, ring-, pellet-, conical-, or saddle-type carrier with an external diameter of 3-15 mm is suitably used.

The supporting of catalytically active material onto the surface of the carrier is carried out by any conventional methods such as penetration or spraying, and preferably by the method of spraying a catalyst slurry onto the carrier heated to 150°-250° C.

3-50 g, preferably 5-15 g of the catalytically active material is supported on 100 cc (apparent volume) of the carrier.

And in the catalyst thus obtained, the total volume of pores having a diameter of 0.05 to 0.45 micron present in the layer of the catalytically active material on the carrier is at least 50%, preferably at least 70%, of that of pores having a diameter of not more than 10 microns present in said layer of the catalytically active material.

Generally, in the case of using a catalyst continuously for a long period of time, the catalytically active material drops off from the surface of the carrier to an increasing extent as the amount of the tetra-alkylbenzene loaded increases. Furthermore, a catalyst is generally prepared by spraying or impregnating a homogenized solution or slurry of the catalytically active material on or in a carrier having high mechanical strength. Since the supporting strength of the catalytically active material is based on a chemical and/or a physical bonding force between the catalytically active material and the carrier, the amount of the catalytically active material to be deposited on the carrier is naturally limited. If it is small, the catalyst has low activity. Even when a catalyst can be obtained which has sufficient activity and contains the catalytically active material with industrially sufficient supporting strength, it frequently happens that the ratio of the catalytically active material which can be supported on the carrier is very low to cause large losses of the catalytically active materials to occur, and therefore, the productivity is poor.

According to this invention, the above problems can be solved by adding whiskers as a supporting aid to the raw materials for the catalytically active material and thereby supporting the catalytically active material well on the carrier.

Metal whiskers and refractory whiskers can, for example, be used suitably as the supporting aid. Examples include metal whiskers such as tungsten, iron or nickel whiskers, and refractory whiskers such as silicon carbide, silicon nitride, aluminum oxide, titanium carbide or calcium phosphate whiskers. Suitable whiskers have an average diameter of not more than 5 microns, preferably not more than 1 micron, a length of not more than 1,000 microns, preferably not more than 500 microns, and an aspect ratio of from 10 to 500, preferably from 20 to 300.

Deposition of the catalytically active material on the carrier can be carried out by conventional known methods. Specifically, it is carried out, for example, by spraying a solution or slurry containing catalytically active ingredients onto the surface of a carrier preheated to 150° to 250° C., or by impregnating the catalyst solution or slurry in the carrier, and concentrating the solution or slurry to adhere the catalytically active material to the carrier. At this time, the whisker is dispersed in the catalyst solution or slurry in an amount of 1 to 20% by weight, preferably 3 to 10% by weight, based on the weight of the finished catalyst. The catalytically active material is supported in a proportion of 3 to 50 g, preferably 5 to 15 g, per 100 cc of the apparent volume of the catalyst.

The supported catalyst of this invention produced by using the whisker as a supporting aid has the advantage of increased activity and/or selectivity in some catalytic reactions because the space volume of the catalyst-supported layer is increased.

The supported material thus obtained is calcined under an air atmosphere at a temperature of 300°-650° C., preferably 400°-600° C. for 1-10 hours, preferably 2-6 hours to get a finished catalyst.

Conventional methods of lowering the temperature of hot spots which appear in the feed gas side of a catalyst bed can be used in order to decrease the reaction with COx and other side reactions of the tetra-alkylbenzene and pyromellitic anhyride and to minimize a thermal deterioration of the catalyst by local heating. For instance, the hot spot temperature is lowered by controlling the amount of reaction in the feed gas side of the catalyst bed.

According to this invention, the above purpose can be achieved by dividing the catalyst packed layer into at least two layers, a catalyst layer on the gas inlet side and a catalyst layer on the gas outlet side, and rendering lower a catalytic activity in the catalyst layer on the gas inlet side. That is, (i) the content of potassium, cesium, rubidium or thallium in the catalytically active material is higher in the catalyst layer on the gas inlet side than in the catalyst layer on the gas outlet side, or (ii) the content of the phosphorus compound in the catalytically active material is lower in the catalyst layer on the gas inlet side than in the catalyst layer on the gas outlet side, or (iii) the surface area of $TiO_2$ and/or $SnO_2$ and/or $ZrO_2$ in the catalytically active material is lower in the catalyst layer on the gas inlet side than in the catalyst layer on the gas outlet side, whereby the amount of reaction in the catalyst layer on the gas inlet side becomes smaller and the hot spot temperature goes lower, providing an excellent method for the production of pyromellitic anhydride. To describe this invention in more detail, the content of the phosphorus compound and the content of the alkali metal or thallium compound in the catalytically active material and the surface area of $TiO_2$ and/or $SnO_2$ and/or $ZrO_2$ are specified as follows. The content of the phosphorus compound, calculated as $P_2O_5$, per 100 parts by weight of $V_2O_5$, $TiO_2$ and/or $SnO_2$ and/or $ZrO_2$ is 0.02 to 1.2 parts by weight in the catalyst layer on the gas inlet side and 0.04 to 10 parts by weight in the catalyst layer on the gas outlet side. The total amount of compounds of alkali metals (Rb, Cs and K) and thallium, calculated as $Rb_2O$, $Cs_2O$, $K_2O$ and $Tl_2O_3$, per 100 parts by weight of $V_2O_5$, $TiO_2$ and/or $SnO_2$ and/or $ZrO_2$ is 0.01 to 1.2 parts by weight in the catalyst layer on the gas inlet side and 0 to 0.8 part by weight in the catalyst layer on the gas outlet side. The surface area of $TiO_2$, $SnO_2$ and $ZrO_2$ is 1 to 40 $m^2/g$ (BET method) in the catalyst layer on the gas inlet side and 5 to 100 $m^2/g$ (BET method) in the catalyst layer on the gas outlet side.

The catalyst with the catalytic activity thus adjusted is loaded, for reaction, to a height of 30 to 70 70 of the whole catalyst packed layer as a catalyst layer on the gas inlet side and to a height of 70 to 30% thereof as a catalyst layer on the gas outlet side.

The catalyst of this invention is used in a multi-tubular fixed bed reactor immersed in a molten salt bath maintained at 320° to 440° C., especially 360° to 420° C. The reaction tube has an inner diameter of 15 to 40 mm, especially 20 to 30 mm.

The catalyst is loaded with multiple layers into the tubes to a total height of 1-5 meters, especially 1.5-3 meters and a feed gas preheated to 120°-160° C. comprising durene or another tetra-alkylbenzene and air or a molecular oxygen-containing gas is introduced into a catalyst bed at a space velocity of 1,000-10,000 $hr^{-1}$ with the ratio of durene or another tetra-alkylbenzene to air 20-60 $g/NM^3$ to obtain pyromellitic anhydride in a yield of 110-120% by weight.

The following examples further illustrate the present invention.

EXAMPLE 1

$TiCl_4$ of special reagent grade (5,700 g) was added to deionized water to form a 60% aqueous solution, and 2,940 g of sulfuric acid of special reagent grade was added to it with stirring. Separately, a saturated aqueous solution containing 3,940 g of ammonium sulfate of special reagent grade and heated at 100° C. was prepared and the saturated solution was stirred into the $TiCl_4$—$H_2SO_4$ aqueous solution. The mixed solution was allowed to stand still to precipitate ammonium titanyl sulfate $(NH_4)_2SO_4.TiOSO_4.H_2O$. The precipitate was filtered and calcined at 750° C. for 10 hours to obtain 2,300 g of powdered $TiO_2$ by thermal decomposition of the ammonium titanyl sulfate.

Oxalic acid (514 g) was dissolved in deionized water to form an aqueous oxalic acid solution. The solution was mixed with 257 g of ammonium metavanadate, 16.2 g of ammonium dihydrogen phosphate and 12.2 g of niobium chloride and thoroughly stirred. To the aqueous solution were added 120 g of antimony trioxide and 1,800 g of aforesaid $TiO_2$, and the mixture was stirred for 30 minutes to form a slurry of a catalytically active material.

Into an externally heatable rotary drum, 2,000 cc of a spherical SiC carrier having an average diameter of 5 mm, an SiC content of 98.5%, and an apparent porosity of 20% was introduced, and preheated to 200°-250° C.

180 g of the catalytically active material was supported on the surface of the carrier by spraying the catalyst slurry onto the carrier while rotating the drum, and subsequently the contents in the drum were calcined at 530° C. for 8 hours under an air atmosphere to obtain a supported catalyst containing $V_2O_5$ and $TiO_2$ in a weight ratio of 10:90 and based on the total weight of $V_2O_5$ and $TiO_2$, 0.5% by weight of $P_2O_5$, 0.3% by weight of $Nb_2O_5$ and 6% by weight of $Sb_2O_3$.

The measurement of the pore distribution of the catalyst thus obtained by the mercury penetration method showed the pore volume occupied by pores with a diameter of 0.05-0.45 micron was 89% of the total volume of pores having a diameter of less than 10 microns.

100 cc of the catalyst was loaded in a stainless tube with an internal diameter of 25 mm immersed in a salt bath maintained at 390° C. Oxidation reaction was carried out by passing hourly 15 g of durene and 500 N-liters of air through the catalyst bed and the product gas was introduced into a crystal collector and a scrubbing vessel.

Analysis of products by liquid chromatography showed that the yield of pyromellitic anhydride was 113.2% by weight.

EXAMPLE 2

A titanium sulfate solution was prepared by mixing ilmenite with 80% sulfuric acid, allowing them to react fully with each other, diluting the reaction product with water to form an aqueous solution of titanium sulfate, adding iron fragments, reducing iron in the ilmenite, and cooling the product to precipitate and separate ferrous sulfate. Hydrous titanium dioxide was prepared by the hydrolysis of the thus obtained titanium sulfate solution while blowing steam kept at 150°-170° C. Hydrous titanium dioxide was calcined under an air atmosphere at 800° C. for 4 hours and pulverized by a jet stream crusher to obtain porous anatase $TiO_2$ having a particle size of about 0.5 micron and a specific surface area of 22 $m^2/g$.

Oxalic acid (1,030 g), 515 g of ammonium metavanadate, 25.9 g of ammonium dihydrogen phosphate, 20.3 g of niobium chloride and 3.4 g of barium nitrate were dissolved in 6400 cc of deionized water and 200 g of antimony trioxide and 1,600 g of $TiO_2$ above prepared were suspended in the solution, and the suspension was homogenized for 30 minutes to get a catalyst slurry.

A catalyst having the catalytic composition, $V_2O_5$:$TiO_2$:$P_2O_5$:$Nb_2O_5$:$Sb_2O_3$:BaO = 20:80:0.8:0.5:10:0.1 by weight, was prepared by the same method as described in Example 1. The volume occupied by pores having a diameter pf 0.05-0.45 micron was 86% of the total volume of pores having a diameter of less than 10 microns.

Pyromellitic anhydride was obtained on the catalyst in a yield of 114.1% by weight under the same conditions as in Example 1 except that the salt bath temperature was changed to 400° C.

EXAMPLES 3-6

Catalysts shown in Table 1 were prepared by the same method as in Example 1 and their performances were shown in Table 2.

TABLE 1

| Example | Catalyst composition (weight ratio) $V_2O_5$:$TiO_2$:$Nb_2O_5$:$P_2O_5$:$Sb_2O_5$ |
|---|---|
| 3 | 10:90:0.5:0.8:15:0.25($Cs_2O$):0.3(SrO):0.1($CeO_2$) |
| 4 | 60:40:0.3:0.5:6:0.1($Rb_2O$):0.08($Tb_4O_7$) |
| 5 | 10:90:0.8:0.8:10:0.07($Tl_2O$):0.3(ZnO) |

TABLE 1-continued

| Example | Catalyst composition (weight ratio) $V_2O_5:TiO_2:Nb_2O_5:P_2O_5:Sb_2O_5$ |
|---|---|
| 6 | 25:75:0.5:1.5:8:0.1($Gd_2O_3$) |

TABLE 2

| Example | N.T. (°C.) | Space velocity ($hr^{-1}$) | Durene concentration ($g/NM^3$) | Yield calculated for pyromellitic anhydride (wt %) |
|---|---|---|---|---|
| 3 | 390 | 8000 | 25 | 114.5 |
| 4 | 390 | 6000 | 35 | 110.2 |
| 5 | 400 | 8000 | 30 | 112.9 |
| 6 | 390 | 5000 | 30 | 113.3 |

EXAMPLE 7

$SnO_2$ having an average diameter of 0.18 micron and a specific surface area of 18 $m^2/g$ was obtained by calcining stannous sulfate at 800° C. for 4 hours and pulverizing it by a jet stream crusher.

Oxalic acid (200 g), 121.8 g of ammonium metavanadate, 15.35 g of ammonium hydrogen phosphate, 19.27 g of niobium chloride and 5.24 g of cesium nitrate were dissolved in 6,400 cc of deionized water and 1,800 g of aforesaid $SnO_2$ was suspended in the solution. The suspension was homogenized to obtain a catalyst slurry.

Into an externally heatable rotatory drum 2,000 cc of a pelletized SiC (5 mm×6 mm L, specific surface area 0.4 $m^2/g$) was introduced and preheated to 150°–200° C. 180 g of the catalytically active material was supported on the carrier by spraying the catalyst slurry on it while rotating the drum and calcining it at 550° C. for 6 hours under an air atmosphere to get catalyst-A.

Separately, catalyst-B was obtained by the same method as in the preparation of catalyst-A except that the amount of ammonium dihydrogen phosphate was changed to 27.63 g.

Into an iron tube (diameter 25 mm, length 3.5 meters) immersed in a salt bath maintained at 410° C, catalyst-B was first loaded to a height of 1.5 meters and subsequently catalyst-A was loaded to a height of 1.5 meters on the catalyst-B.

From the top of the tube a mixed gas preheated to 140° C. and having a durene/air ratio of 30 $g/NM^3$ was introduced at a space velocity of 4,000 $hr^{-1}$ to obtain pyromellitic anhydride in a yield of 113.4% by weight.

EXAMPLE 8

A hydrogen chloride solution (200 cc), 10 g of vanadium pentoxide, 1.62 g of ammonium dihydogen phosphate and 0.28 g of potassium sulfate were dissolved in 800 cc of deionized water. Stannous sulfate (42.74 g) and 60 g of porous anatase $TiO_2$ (diameter 0.5 micron, specific surface area 20 $m^2/g$) were suspended in the solution, and the suspension was homogenized by a mixer to obtain a catalyst slurry.

Into an externally heatable evaporating dish the slurry obtained above and 1,000 cc of a spherical carrier (diameter 6 mm, specific surface area 0.3 $m^2/g$, apparent porosity 48%) comprising 75% by weight of SiC, 17% by weight of $SiO_2$, and 8% by weight of $Al_2O_3$ were introduced and heated to dryness under mixing to support 160 g of the catalytically active material on the carrier. The contents of the dish were calcined at 580° C. for 8 hours to obtain a catalyst.

In a carbon steel tube (diameter 20 mm, 3.5 meters L) immersed in a salt bath maintained at 405° C., the catalyst was loaded to a height of 2.5 meters and a mixed gas having a durene/air ratio of 40 $g/NM^3$ was introduced at a space velocity of 3,000 $hr^{-1}$ to obtain pyromellitic anhydride in a yield of 112.1% by weight.

EXAMPLE 9

Oxalic acid (120 g), 55.7 g of vanadium pentoxide, 56.1 g of niobium chloride, 9.02 g of ammonium hydrogen phosphate, 7.2 g of rubidium sulfate and 2.33 g of thallium sulfate were dissolved in 6,400 cc of deionized water, and 930 g of $SnO_2$ used in Example 7 and 870 g of $TiO_2$ used in Example 8 were suspended in the solution, and the suspension was homogenized by mixer to obtain a catalyst slurry.

Into an externally heatable rotatory drum 2,000 cc of a ring-type carrier (apparent porosity 40%, external diameter 7 mm, internal diameter 4 mm, length 7 mm) comprising 10% by weight of magnesium silicate, 20% by weight of $SiO_2$, and 70% by weight of SiC was introduced and preheated to 150°–200° C. 150 g of the catalytically active material was supported on the carrier by spraying the slurry on it under rotating and the contents of the drum were calcined at 500° C. for 4 hours to obtain catalyst-C.

Separately, catalyst-D was prepared by the same method as in the preparation of catalyst-C except that rubidium sulfate and thallium sulfate were not added.

Into a carbon steel reactor (ID=25 mm, L=3.5 mm) immersed in a salt bath maintained at 380° C., catalyst-D was first loaded to a height of 1,000 mm and onto it catalyst-C was loaded to a height of 1,000 mm.

From the top of the tube a mixed gas of durene and a molecular oxygen-containing gas (oxygen 10% by volume, steam 10% by volume, nitrogen 80% by volume) of which the ratio of durene/molecular oxygen-containing gas was 40 $g/NM^3$ was introduced at a space velocity of 3,500 $hr^{-1}$ to obtain pyromellitic anhydride of 117.3% by weight.

EXAMPLE 10

$ZrO_2$ having a particle size of 0.2 micron and a specific surface area of 25 $m^2/g$ was obtained by calcining zirconyl nitrate at 750° C. for 3 hours and pulverized it by a jet stream crusher.

Oxalic acid (200 g), 96.7 g of ammonium metavanadate, 9.1 g of ammonium dihydrogen phosphate, 22.9 g of niobium chloride, 3.47 g of potassium hydroxide were dissolved in 6,400 cc of deionized water, and 1,800 g of $ZrO_2$ above obtained was suspended in the solution. The suspension was homogenized by a mixer to get a catalyst slurry.

Into an externally heatable rotatory drum 2,000 cc of a ring-type carrier (ID=4 mm, OD=6 mm, L=6 mm, specific surface area=0.2 $m^2/g$) comprising 6% by weight of $SiO_2$, 2% by weight of $Al_2O_3$, and 92% by weight of SiC was introduced and preheated to 150°–220° C. 180 g of the catalytically active material was supported on the carrier by spraying the catalyst slurry on it while rotating the drum and the contents of the drum were calcined at 540° C. for 6 hours to obtain a catalyst.

Into a carbon steel tube (ID=25 mm, L=3.5 meters) immersed in a salt bath maintained at 400° C. the catalyst was loaded to a height of 2,500 mm. From the top of the tube, a preheated mixed gas having a durene/air ratio of 25 $g/NM^3$ was introduced at a space velocity of 4,000 hr$^{-1}$. The initial yield of pyromellitic anhydride was 114.5% by weight and the hot spot temperature was 465° C.

The yield and hot spot temperature after 3 months and 6 months continuation of oxidation reaction under the above conduitions were 114.1% by weight, 466° C. (3 months) and 113.3% by weight, 461° C. (6 months), respectively. These results show the very stable activity of the catalyst in a long run.

EXAMPLE 11

Oxalic acid (450 g), 201.4 g of ammonium metavanadate, 23.8 g of niobium chloride, 9.5 g of ammonium dihydrogen phosphate, and 3.38 g of cesium nitrate were dissolved in 6,400 cc of deionized water, and 980 g of $ZrO_2$ (particle size 0.2 micron, specific surface area 25 m$^2$/g) and 820 g of porous anatase $TiO_2$ (particle size 0.5 micron, specific surface area 20 m$^2$/g) were suspended in the solution to obtain catalyst slurry.

Into an externally heatable rotatory drum 2,000 cc of a spherical catalyst (diameter 6 mm, apparent porosity 43%, surface area 0.3 m$^2$/g) comprising 2% by weight of $Al_2O_3$, 4% by weight of $SiO_2$ and 94% by weight of SiC was introduced and preheated to 150°–200° C.

180 g of the catalytically active material was supported by spraying the catalyst slurry on it. The contents of the drum were calcined at 520° C. for 4 hours to obtain catalyst-E.

Separately, catalyst-F was prepared by the same method as in catalyst-E except that $ZrO_2$ (particle size 0.3 micron, specific surface area 12 m$^2$/g) and porous anatase $TiO_2$ (particle size 0.6 micron, surface area 13 m$^2$/g) were used.

Catalyst-E was first loaded into a tube (ID=25 mm, 3.5 meters L) immersed in a salt bath maintained at 400° C. to a height of 1.5 meters and subsequently catalyst-F was loaded to a height of 1 meter on it.

From the top of the tube a mixed gas having a durene/air ratio of 35 g/NM$^3$ was introduced at a space velocity of 4,000 hr$^{-1}$ to obtain pyromellitic anhydride in a yield of 115.6% by weight.

EXAMPLE 12

Oxalic acid (900 g), 408.6 g of ammonium metavanadate, 4.3 g of niobium chloride, 27.4 g of ammonium dihydrogen phosphate, 21.3 g of thallium nitrate were dissolved in 6,400 cc of deionized water and 42.4 g of antimony trioxide, 720 g of $ZrO_2$ (same to Example 11) and 1,080 g of $TiO_2$ (same to Example 11) were suspended in the solution to obtain a catalyst slurry.

Into an externally heatable drum 2,000 cc of a spherical self-bonded SiC carrier (diameter 6 mm, apparent porosity 38%, specific surface area 0.2 m$^2$/g) was introduced and pre-heated to 150°–200° C. 170 g of the catalytically active material was supported on the carrier and the contents of the drum were calcined at 580° C. for 3 hours to obtain catalyst-G.

Separately, catalyst-H was prepared by the same method as in the preparation of catalyst-G except that 6.68 g of rubidium nitrate was used instead of thallium nitrate.

Catalyst-H was first loaded into a tube (ID=25 mm, L=3.5 meters) immersed in a salt bath maintained at 375° C. to a height of 1.25 meters and subsequently on it catalyst-G was loaded to a height of 1.25 meters.

From the top of the tube, a mixture of durene and a molecular oxygen-containing gas (oxygen 12%, steam 10%, nitrogen 78%) of which the ratio of durene to the oxygen-containing gas was 40 g/NM$^3$ was introduced at a space velocity of 3,500 hr$^{-1}$. The initial yield of pyromellitic anhydride was 117.1% by weight and the hot spot temperature was 457° C.

The salt bath temperature was raised to, and maintained at, 387° C. for 1 month so that the hot spot temperature became 500° C. When the salt bath temperature was lowered to 375° C. after this period, the yield and hot spot temperature at that time were 116.2% by weight and 452° C. respectively, and no serious thermal deterioration was observed.

EXAMPLE 13

Oxalic acid (200 g), 96.5 g of ammonium metavanadata, 7.6 g of niobium chloride, 20.7 g of cesium nitrate were dissolved in 6,400 cc of deionized water and 18.8 g of antimony trioxide, 940 g of $ZrO_2$ (same as that in Example 10) and 470 g of $TiO_2$ (same as that in catalyst-F of Example 11) and 390 g of $SnO_2$ obtained by calcination of $SnSO_4$ at 700° for 4 hours were suspended in the solution to obtain a catalyst slurry.

Into an externally heatable drum 2,000 cc of an interlock saddle-type carrier (apparent porosity 45%, specific surface area 0.4 m$^2$/g, average length 12 mm, external diameter 5 mm, internal diameter 6 mm, thickness 1 mm) comprising 80% by weight of SiC, 6% by weight of MgO and 14% by weight of $SiO_2$ was introduced and preheated to 150°–200° C. 160 g of the catalytically active material was supported by spraying the catalyst slurry on it while rotating the drum and the contents of the drum were calcined under an air atmosphere at 520° C. for 4 hours to obtain catalyst-I.

Separately, catalyst-J was prepared by the same method as in catalyst-I except that cesium nitrate was not added.

Into a carbon steel tube (ID=20 mm, L=4.5 meters) immersed in a salt bath maintained at 380° C., catalyst-J was first loaded to a height of 2,000 mm and onto it catalyst-I was loaded to a height of 2,000 mm.

From the top of the tube a 4-isopropylpseudocumene/air mixture of which the ratio of 4-isopropylpseudocumene/air was 40 g/NM$^3$ was introduced at a space velocity of 3,500 hr$^{-1}$ to obtain pyromellitic anhydride in a yield of 98.7% by weight.

EXAMPLE 14

$TiCl_4$ of special reagent grade (5,700 g) was gradually added dropwise to water to form a 60% aqueous solution. Sulfuric acid of special reagent grade (2,940 g) was added to the $TiCl_4$ aqueous solution with stirring. Separately, a saturated aqueous solution containing 3,940 g of ammonium sulfate of special reagent grade and heated to 100° C. was prepared, and added to the $TiCl_4$—$H_2SO_4$ aqueous solution with stirring. The mixture was then left to stand to precipitate ammonium titanyl sulfate [$(NH_4)_2.SO_4.TiOSO_4.H_2O$]. The precipitate was separated by filtration, and calcined at 750° C. for 10 hours to obtain 2,300 g of $TiO_2$.

Oxalic acid (514 g) was dissolved in 6,400 cc of deionized water to form an oxalic acid solution, and 120 g of antimony trioxide and an aqueous solution of hydrogen chloride containing 257 g of ammonium vanadate, 16.2 g of ammonium dihydrogen phosphate and 12.2 g of niobium chloride were added to the oxalic acid solution. To the resulting solution were added 120 g of silicon nitride whiskers having a diameter of 0.5 micron, and an average length of 180 microns and 1,800 g of $TiO_2$ mentioned above, and the mixture was stirred for 30 minutes to form a catalyst slurry.

Two thousand cc of an SiC carrier having an average particle diameter of 5 mm, an apparent porosity of 20% and an SiC content of 98.5% was introduced into an externally heatable rotatory drum, and preheated to 200 to 250° C. While the rotatory drum was rotated, the catalyst slurry was sprayed onto the carrier to deposit 180 g of the catalytically active material, and then calcined in air at 530° C. for 8 hours. The finished catalyst had the following composition by weight.

$V_2O_5:TiO_2:P_2O_5:Nb_2O_5:Sb_2O_3 = 10:90:0.5:0.3:6$

The whisker content of the catalyst was 6% by weight based on the weight of the catalytically active material. The ratio of the catalytically active material effectively supported on the carrier based on its amount originally used was 94%.

Measurement of the pore distribution of the finished catalyst by a porosimeter in accordance with the mercury penetration method showed that the volume of pores having a diameter of 0.05 to 0.45 micron is 93% of the total volume of pores having a diameter of not more than 10 microns.

A stainless steel reaction tube having a diameter of 25 mm was filled with 100 cc of the resulting catalyst, and immersed in a molten salt bath kept at 390° C. Fifteen grams of durene and 500 Nl of air were passed hourly through the reaction tube and reacted. The reaction gas was conducted to a crystal collector and a scrubbing vessel to collect the product. The entire product collected was dissolved in warm water and analyzed. It was found that pyromellitic acid was obtained in a yield of 114.8% calculated as pyromellitic anhydride.

When the above procedure was repeated without adding the whiskers, the ratio of the catalytically active material effectively supported on the carrier was 63%, and the yield of pyromellitic anhydride was 113.2%.

EXAMPLE 15

Zirconyl nitrate was thermally decomposed at 750° C. for 3 hours to obtain $ZrO_2$ having a specific surface area of 25 m$^2$/g. $ZrO_2$ was finely pulverized to an average particle diameter of 0.2 micron and used as a catalyst material.

Oxalic acid (200 g) was dissolved in 6,400 cc of deionized water, and 96.7 g of ammonium metavanadate, 9.1 g of ammonium dihydrogen phosphate, 22.9 g of niobium chloride and 3.47 g of potassium hydroxide were added. Furthermore, 75 g of silicon carbide whiskers having a diameter of 0.2 micron and a length of 20 microns were added. The mixture was thoroughly stirred, and 1,800 g of the finely pulverized $ZrO_2$ prepared above was added by using an emulsifier, a catalyst slurry was obtained.

Two thousand cc of a ring-like carrier composed of 2% by weight of $Al_2O_3$, 6% by weight of $SiO_2$ and 92% by weight of SiC and having an apparent porosity of 45%, a specific surface area of 0.2 m$^2$/g, an average inside diameter of 4 mm, an average outside diameter of 6 mm and an average length of 6 mm was introduced into an externally heatable rotatory drum, and preheated to 150° to 200° C. The catalyst slurry prepared above was sprayed onto the carrier to deposit 180 g of the catalytically active material, and calcined in air at 540° C. for 6 hours to obtain a catalyst. The whisker content of the catalsyt was 4% by weight based on the catalytically active material. The ratio of the catalytically active material effectively supported was 95%.

The resulting catalyst was filled to a height of 2.5 m in an iron reaction tube, 25 mm in inside diameter and 3.5 m in length, immersed in a molten salt bath kept at 400° C.

A gaseous mixture of durene and air having a durene/air ratio of 25 g/NM$^3$ was preheated to 140° C., and passed into the reactor from its top at a space velocity of 4,000 hr$^{-1}$ (STP). Pyromellitic anhydride was obtained in an initial yield of 115.5% by weight. The hot spot temperature was 461° C.

Under these conditions, the reaction was continued, and the hot spot temperature and the yield were measured at the end of 3 months and 6 months, respectively, and found to be 462° C. and 115.4%, and 457° C. and 115.0% by weight.

The activity of the catalyst was stable during this operation over extended periods of time.

When a catalyst was prepared in the same way as above except that the whiskers were not added, the ratio of the catalytically active material effectively supported was 64%. When the same reaction as above was carried out using the resulting catalyst, the initial yield of pyromellitic anhydride was 114.5% by weight, and hot spot temperature was 465° C. When the reaction was continued under these conditions, the hot spot temperature and the yield of the product were 466° C. and 114.1% by weight, and 461° C. and 113.3% by weight at the end of 3 months and 6 months, respectively.

EXAMPLE 16

Oxalic acid (514 g) was dissolved in 6,400 cc of deionized water to form an aqueous oxalic acid solution. The solution was mixed with an aqueous hydrochloric acid solution containing 257 g of ammonium vanadate, 16.2 g of ammonium dihydrogen phosphate and 20.3 g of niobium chloride, 9.5 g of rubidium nitrate and 30 g of antimony trioxide. To the resulting solution were added 120 g of silicon carbide whiskers having a diameter of 0.2 micron and a length of 20 microns and 1,800 g of $TiO_2$ formed in Example 14. The mixture was stirred for 30 minutes to form a catalyst slurry.

Into an externally heatable rotatory drum, 2,000 cc of a SiC carrier (SiC content 98.5%) having an average particle size of 6 mm and an apparent porosity of 20% was introduced and preheated to a temperature of 150° to 200° C. While rotating the drum, the catalyst slurry was sprayed onto the carrier to support 180 g of the catalytically active material, and calcined in air at 550° C. for 5 hours to obtain catalyst-K. The catalyst had the following composition by weight.

$V_2O_5:TiO_2:P_2O_5:Nb_2O_5:Sb_2O_3:Rb_2O = 10:90:0.5:0.5:1.5:0.30$

Separately catalyst-L was obtained in the same way as above except that the amount of rubidium nitrate was changed to 1.58 g. The catalyst had the following composition.

$V_2O_5:TiO_2:P_2O_5:Nb_2O_5:Sb_2O_3:Rb_2O = 10:90:0.5:0.5:1.5:0.05$

The whisper content was 6% by weight based on the catalytically active material in each catalyst.

Into an iron reaction tube having an inner diameter of 25 mm and a length of 3.0 m and immersed in a molten salt bath maintained at 390° C., catalyst-L was first loaded to a height of 1.0 m and onto it catalyst-K was then loaded to a height of 1.0 m.

From the top of the reaction tube, a durene/air mixture having a durene/air ratio of 30 g/NM$^3$ was introduced at a space velocity of 5,000 hr$^{-1}$ (STP). Pyromellitic anhydride was obtained in an initial yield of 115.2% by weight. The hot spot temperature was 442° C.

Under these conditions, the reaction was continued, and the hot spot temperature and the yield were measured at the end of 3 months and 6 months respectively, and found to be 440° C. and 115.1% by weight, and 439° C. and 115.0% by weight.

EXAMPLE 17

Hydrochloric acid (200 cc) was dissolved in 800 cc of water, and the solution was mixed with 8 g of vanadium pentoxide, 0.49 g of ammonium dihydrogen phosphate, 6.1 g of niobium chloride, 0.13 g of cesium nitrate and 2.0 g of antimony trioxide, followed by thoroughly stirring them. To the solution were added 45.6 g of stannous sulfate and 60 g of porous anatase TiO$_2$ having an average particle size of 0.5 micron and a specific surface area of 20 m$^2$/g. The mixture was formed into a catalyst slurry by an emulsifier.

Into an externally heatable evaporation plate, the above catalyst slurry and 1,000 cc of a spherical porous carrier having an apparent porosity of 48%, a specific surface area of 0.3 m$^2$/g and an average diameter of 6 mm and comprising 8%, as Al$_2$O$_3$, of aluminum, 75% of SiC and 17% of SiO$_2$. While stirring the carrier, 160 g of the catalytically active material was concentrated and deposited on the carrier, and calcined in air at 560° C. for 6 hours to obtain catalyst-M. The catalyst had the following composition.

$$V_2O_5:TiO_2:SnO_2:P_2O_5:Nb_2O_5:Sb_2O_3:Cs_2O = 8:60:32:0.3:3:2:0.1$$

Separately, catalyst-N was formed as in the preparation of catalyst-M except that the amount of cesium sulfate was changed to 0.07 g. The catalyst had the following composition.

$$V_2O_5:TiO_2:P_2O_5:Nb_2O_5:Sb_2O_3:Cs_2O = 8:92:0.3:3:2:0.05$$

Into a tube having an inner diameter of 20 mm and a height of 3.5 m and immersed in a molten salt bath maintained at 405° C., catalyst-N was first loaded to a height of 1.6 m and onto it catalyst-M was then loaded to a height of 2.4 m.

From the top of the tube, a gas mixture having a durene/air ratio of 40 g/NM$^3$ was introduced at a space velocity of 3,000 hr$^{-1}$ (STP). Pyromellitic anhydride was obtained in an initial yield of 113.1% by weight. The hot spopt temperature was 456° C.

Under these conditions, the reaction was continued, and the hot spot temperature and the yield were measured at the end of 3 months and 6 months respectively, and found to be 455° C. and 112.9% by weight, and 454° C. and 112.8% by weight.

EXAMPLE 18

Oxalic acid (514 g) was dissolved in 6,400 cc of deionized water to form an aqueous oxalic acid solution. The solution was mixed with 386 of ammonium vanadate, 32.4 g of ammonium dihydrogen phosphate, 20.3 g of niobium chloride, 5.6 g of potassium sulfate, 2.05 g of cesium sulfate and 80 g of antimony trioxide. To the resulting solution were added 120 g of silicon carbide whiskers having a diameter of 0.6 micron and a length of 50 microns and 1,700 g of TiO formed in Example 14. The mixture was stirred for 30 minutes to form a catalyst slurry.

Into an externally heatable rotatory drum, 2,000 cc of a SiC carrier having an average particle size of 6 mm, an apparent porosity of 38% and a specific surface area of 0.2 m$^2$/g was introduced and preheated to a temperature of 150° to 200° C. While rotating the drum, the catalyst slurry was sprayed onto the carrier to support 170 g of the catalytically active material, and calcined in air at 580° C. for 3 hours to obtain catalyst-O. The catalyst had the following composition by weight.

$$V_2O_5:TiO_2:P_2O_5:Nb_2O_5:Sb_2O_3:K_2O:Cs_2O = 15:85:1.0:0.5:4.0:0.15:0.08$$

Separately, catalyst-P was formed in the same way as in the preparation of catalyst-O except that the amounts of potassium sulfate and cesium sulfate were changed to 1.9 g and 1.28 g respectively. The catalyst had the following composition.

$$V_2O_5:TiO_2:P_2O_5:Nb_2O_5:Sb_2O_3:K_2O:Cs_2O = 15:85:1.0:0.5:4.0:0.05:0.05$$

The whisker content was 6% by weight based on the catalytically active material in each catalyst.

Into an iron reaction tube having an inner diameter of 25 mm and a height of 3.5 m and immersed in a molten salt bath maintained at 380° C., catalyst-P was first loaded to a height of 1.25 m and onto it catalyst-O was then loaded to a height of 1.25 m.

From the top of the reaction tube, a gas mixture having a durene/molecular oxygen-containing gas (comprising 12% by volume of oxygen, 10% by volume of vapor and 78% by volume of nitrogen) ratio of 40 g/NM$^3$ was introduced at a space velocity of 3,500 hr$^{-1}$ (STP). Pyromellitic anhydride was obtained in an initial yield of 117.5%. The hot spot temperature was 445° C.

Under these conditions, the reaction was continued, and the hot spot temperature and the yield were measured at the end of 3 months and 6 months respectively, and found to be 443° C. and 117.2% by weight, and 442° C. and 117.1% by weight.

EXAMPLE 19

Oxalic acid (900 g) was dissolved in 6,400 cc of water. The solution was mixed with 233.1 g of ammonium vanadate, 6.2 g of ammonium dihydrogen phosphate, 1.97 g of niobium pentachloride and 14.3 g of thallium sulfate, followed by thoroughly stirring them. To the solution were added 680 g of ZrO$_2$ (particle size 0.3 micron, specific surface area 10 m$^2$/g) and 1,020 g of TiO$_2$ (particle size 0.6 micron, specific surface area 15 m$_2$/g), and the mixture was formed into a catalyst slurry by an emulsifier.

Into an externally heatable rotatory drum, 2,000 cc of a porous ring-like carrier having an apparent porosity of 40%, an average outer diameter of 7 mm, an average inner diameter of 4 mm and an average length of 7 mm and comprising 10% by weight of MgO, 20% by weight of SiO$_2$ and 70% by weight of SiC was introduced and preheated to a temperature of 150° to 200° C. The above slurry was sprayed onto the carrier to support 150 g of the catalytically active material, and calcined in air at 560° C. for 6 hours to afford catalyst-Q. The catalyst had the following composition by weight.

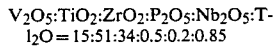
$V_2O_5:TiO_2:ZrO_2:P_2O_5:Nb_2O_5:Tl_2O = 15:51:34:0.5:0.2:0.85$

Separately, catalyst-R was obtained in the same way as in the preparation of catalyst-Q except $ZrO_2$ (particle size 0.1 micron, specific surface area 30 m$^2$/g) and $TiO_2$ (particle size 0.4 micron, specific surface area 25 m$^2$/g) were used and the amount of thallium sulfate was changed to 8.42 g. The catalyst had the following composition.

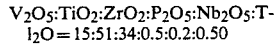
$V_2O_5:TiO_2:ZrO_2:P_2O_5:Nb_2O_5:Tl_2O = 15:51:34:0.5:0.2:0.50$

Into an iron reaction tube having an inner diameter of 25 mm and a height of 3.5 m and immersed in a molten salt bath maintained at 380° C., catalyst-R was first loaded to a height of 1.25 m and onto it catalyst-Q was then loaded to a height of 1.25 m. The reaction was performed under the same reaction conditions as in Example 18. In consequence, pyromellitic anhydride was obtained in an initial yield of 116.8% by weight. The hot spot temperature was 441° C.

Under these conditions, the reaction was continued, and the hot spot temperature and the yield were measured at the end of 3 months and 6 months respectively, and found to be 440° C. and 116.5% by weight, and 439° C. and 116.4% by weight.

EXAMPLE 20

Catalyst-S was formed in the same way as in Example 10 except using a ring-like carrier (inner diameter 6 mm, outer diameter 8 mm, length 6 mm, specific surface area 0.2 m$^2$/g) comprising 6% of $SiO_2$, 2% of $Al_2O_3$ and 92% of SiC.

Into an iron reaction tube having an inner diameter of 25 mm and a length of 3.5 m and immersed in a molten salt bath maintained at 400° C., the same catalyst as obtained in Example 10 was first loaded to a height of 1.0 m and onto it catalyst-S was then loaded to a height of 1.5 m.

From the top of the reaction tube, a gas mixture having a durene/air ratio of 25 g/NM$^3$ was introduced at a space velocity of 4,000 hr$^{-1}$ (STP). Pyromellitic anhydride was obtained in an initial yield of 115.0% by weight. The hot spot temperature was 455° C.

Under these conditions, the reaction was continued, and the hot spot temperature and the yield were measured at the end of 3 months and 6 months respectively, and found to be 454° C. and 114.5%, and 452° C. and 114.0% by weight.

What we claim is:

1. In a method for the preparation of pyromellitic acid or its anhydride by catalytic vapor phase oxidation of a tetra-$C_1$-$C_4$-alkylbenzene using a catalyst comprising catalytically active material composed of 1 to 20 parts by weight of $V_2O_5$, 99 to 80 parts by weight of $TiO_2$ and/or $SnO_2$ and/or $ZrO_2$, and per 100 parts by weight of $V_2O_5$, $TiO_2$ and/or $SnO_2$ and/or $ZrO_2$, 0.02 to 10 parts by weight, calculated as $P_2O_5$, of phosphorus compound, 0.01 to 5 parts by weight, calculated as $Nb_2O_5$, of a niobium compound, 0 to 1.2 parts by weight, calculated as oxide, of at least one metal selected from the group consisting of potassium, cesium, rubidium and thallium, and 0 to 10 parts by weight, calculated as $Sb_2O_3$, of an antimony compound, and an inert carrier supporting said catalytically active material thereon, the improvement in which said catalyst is divided into at least two layers, a layer on the gas inlet side and a layer on the gas outlet side, and (i) the content of posassium, cesium, rubidium or thallium is higher in the catalyst layer on the gas inlet side than in the catalyst layer on the gas outlet side, wherein the total amount of potassium, cesium, rubidium and thallium, calculated as $K_2O$, $Cs_2O$, $Rb_2O$ and $Tl_2O_3$, respectively, is 0.01 to 1.2 parts by weight in the catalyst layer on the gas inlet side and 0 to 0.8 part by weight in the catalyst layer on the gas outlet side, or (ii) the content of the phosphorus compound is lower in the catalyst layer on the gas inlet side than in the catalyst layer on the gas outlet side, wherein the content of the phosphorus compound calculated as $P_2O_5$ is 0.02 to 1.2 parts by weight in the catalyst layer on the gas inlet side and 0.04 to 10 parts by weight in the catalyst layer on the gas outlet side, or (iii) the surface area of $TiO_2$ and/or $SnO_2$ and/or $ZrO_2$ is lower in the catalyst layer on the gas inlet side than in the catalyst layer on the gas outlet side, wherein the surface area of $TiO_2$, $SnO_2$ and $ZrO_2$ is 1 to 40 m$^2$/g in the catalyst layer on the gas inlet side and 5 to 100 m$^2$/g in the catalyst layer on the gas outlet side.

2. The method of claim 1 wherein said inert carrier is porous and has an alumina content of not more than 10% by weight and a silicon carbide content of at least 50% by weight.

3. The method according to any one of claims 1 or 2 wherein said catalyst is prepared by using 1 to 20% by weight of the catalytically active material, of whiskers having an average diameter of not more than 5 microns and an aspect ratio of from 10 to 500 as a supporting aid.

4. The method of claim 1 wherein said inert carrier has an apparent porosity of 5 to 50% and a specific surface area of less than 5 m$^2$/g.

5. The method of claim 4 wherein the inert carrier comprises more than 50% by weight of silicon carbide.

6. The method of claim 4 or 5 wherein from 3 to 50 grams of the catalytically active material is supported on 100 cubic centimeters of the inert carrier.

7. The method of claim 6 where from 5 to 15 grams of the catalytically active material is supported on 100 cubic centimeters of the inert carrier.

8. The method of claim 3 wherein the whiskers are formed from a metal or refractory material selected from the group consisting of tungsten, iron, nickel, silicon carbide, silicon nitride, aluminum oxide, titanium carbide and calcium phosphate.

9. The method of claim 1 wherein the catalyst layer on the gas inlet side comprises from 30 to 70% of the total catalyst layer and the catalyst layer on the gas outlet side comprises from 70 to 30% by weight of the total catalyst layer.

10. The method of claim 1 wherein the tetra-$C_1$-$C_4$-alkylbenzene is durene.

11. The method of claim 10 wherein the catalyst layers on the gas inlet side and gas outlet side have a total height of from 1 to 5 meters and wherein a feed gas containing durene and a molecular oxygen-containing gas at a temperature of 120° to 160° C. is introduced into the catalyst bed at a space velocity of 1,000–10,000 hr$^{-1}$.

12. The method of claim 1 wherein the condition (i) is satisfied.

13. The method of claim 1 wherein the condition (ii) is satisfied.

14. The method of claim 1 wherein the condition (iii) is satisfied.

* * * * *